US006512140B1

(12) United States Patent
Liu et al.

(10) Patent No.: US 6,512,140 B1
(45) Date of Patent: Jan. 28, 2003

(54) PROCESS FOR THE PREPARATION OF 1-(MERCAPTOMETHYL)-CYCLOPROPANEACETIC ACID

(75) Inventors: Lu Wei Liu, Kirkland (CA); Yuan Wang, Kirkland (CA); Hérika Marrugo, Verdun (CA); Sylvain Harper, Pointe-Claire (CA); David D. C. Quan, LaSalle (CA); Zhihong (Nancy) Zhou, Kirkland (CA); Gregory Bydlinski, Montreal (CA)

(73) Assignee: Delmar Chemicals Inc., La Salle (CA)

( * ) Notice: Subject to any disclaimer, the term of this patent is extended or adjusted under 35 U.S.C. 154(b) by 0 days.

(21) Appl. No.: 10/122,541

(22) Filed: Apr. 15, 2002

(30) Foreign Application Priority Data

Feb. 6, 2002 (CA) .............................................. 2371048

(51) Int. Cl.[7] .............................................. C07L 61/04
(52) U.S. Cl. ...................... 562/506; 564/191; 549/330; 549/434; 549/439
(58) Field of Search ...................... 562/506; 564/191; 549/330, 434, 439

(56) References Cited

U.S. PATENT DOCUMENTS

| 5,270,324 A | 12/1993 | Zamboni et al. |
| 5,472,964 A | 12/1995 | Young et al. |
| 5,523,477 A | 6/1996 | King et al. |
| 5,534,651 A | 7/1996 | Quittmann et al. |

FOREIGN PATENT DOCUMENTS

| EP | 0 480 717 B1 | 4/1992 |
| EP | 0 641 775 B1 | 3/1995 |
| WO | WO 95/18132 | 7/1995 |

OTHER PUBLICATIONS

Pinner, et al., Umwandlung der Nitrile in Imide, Ber. 10, 1889 (1877).
Pinner, et al., Umwandlung der Nitrile in Imide, Ber. 11, 1475 (1878).
Pinner, Uebor die Umwandlung der Nitrile in Imide, Ber. 16, 1643 (1883).
Neilson, Douglas G., in Patai, "The Chemistry of Amidines and Imidates, " pp. 385–489, Wiley, New York (1975).

Primary Examiner—Paul J. Killos
(74) Attorney, Agent, or Firm—Kirkpatrick & Lockhart LLP

(57) ABSTRACT

A process for the preparation of highly pure 1-(mercaptomethyl)-cyclopropaneacetic acid is described. Treatment of 1-(hydroxymethyl)-cyclopropaneacetonitrile with an acid provides the corresponding imino ester and/or halo-amide, which when reacted with thiourea provide the corresponding amide-isothiuronium salt. Hydrolysis of the amide-isothiuronium salt followed by an in situ oxidation allows the facile isolation and purification of 1-[1-(carboxymethyl)-cyclopropanemethyldisulfanylmethyl]-cyclopropaneacetic acid (also known as 1-(mercaptomethyl)-cyclopropaneacetic acid disulfide). Reduction of the 1-(mercaptomethyl)-cyclopropaneacetic acid disulfide under mild conditions provides the 1-(mercaptomethyl)-cyclopropaneacetic acid with high purity.

18 Claims, No Drawings

PROCESS FOR THE PREPARATION OF 1-(MERCAPTOMETHYL)-CYCLOPROPANEACETIC ACID

FIELD OF THE INVENTION

The invention relates to novel processes and intermediates for preparing 1-(mercaptomethyl)-cyclopropaneacetic acid.

BACKGROUND OF THE INVENTION

The compound 1-(mercaptomethyl)-cyclopropaneacetic acid and its derivatives are important intermediates for the synthesis of leukotriene antagonists, which are useful in the treatment of asthma and other conditions mediated by leukotrienes, such as inflammation and allergies. A number of leukotriene antagonists are described in European Patent Nos. 480,717 and 604,114, and U.S. Pat. No. 5,270,324. Among the compounds disclosed in these patents are those which include a thiomethylcyclopropaneacetic acid moiety. This moiety is introduced using derivatives of 1-(mercaptomethyl)-cyclopropaneacetic acid.

A number of methods for preparing 1-(mercaptomethyl)-cyclopropaneacetic acid are known, for example in U.S. Pat. Nos. 5,523,477 and 5,534,651. Most known syntheses for preparing 1-(mercaptomethyl)-cyclopropaneacetic acid use either thiolacetic acid or hydrogen sulfide derivatives to introduce the mercapto function. Due to their strong disagreeable odour, the manipulation of these reagents and the corresponding synthetic intermediates is technically demanding. Further, essentially all the key intermediates in these syntheses are liquids or oils, which require either vacuum distillation or column chromatography for purification. In addition, the final step of each of these syntheses involves a hot basic hydrolysis in which the temperature may range from 80° C. to aqueous reflux. Since 1-(mercaptomethyl)-cyclopropaneacetic acid is sensitive to oxidation, the use of such harsh reaction conditions may lead to reduced yields and/or product of unacceptable purity.

Therefore, the need exists for an improved process for preparing 1-(mercaptomethyl)-cyclopropaneacetic acid.

SUMMARY OF THE INVENTION

In one aspect, the present invention provides a novel process for the preparation of 1-(mercaptomethyl)-cyclopropaneacetic acid which avoids the above-described disadvantages of known processes. In the process of the present invention, 1-(mercaptomethyl)-cyclopropaneacetic acid is prepared from 1-(hydroxymethyl)-cyclopropaneacetonitrile, which is commercially available or can be prepared by known methods from readily available reagents.

The process of the present invention essentially comprises four steps, the first step being the conversion of 1-(hydroxymethyl)-cyclopropaneacetonitrile to 5-oxa-spiro[2.4]hept-6-ylideneamine (also referred to herein as the "imino ester") and acid addition salts thereof, which may be partially or totally converted to 1-(halomethyl)-cyclopropaneacetamide (also referred to herein as the "halo-amide") under the reaction conditions.

The imino ester and halo-amide intermediates are preferably not isolated, but are reacted in situ with thiourea in the second step of the process to give the novel intermediate 1-(carbamimidoylsulfanylmethyl)-cyclopropaneacetamide, which is preferably isolated in the form of a solid acid addition salt, and optionally purified prior to further reaction.

In the third step of the process, 1-(carbamimidoylsulfanylmethyl)-cyclopropaneacetamide, or a salt thereof, is subjected to basic hydrolysis followed by oxidation in situ to form the disulfide of 1-(mercaptomethyl)-cyclopropaneacetic acid, a solid, which is preferably isolated and purified.

In the fourth and final step, the disulfide is reduced to 1-(mercaptomethyl)-cyclopropaneacetic acid.

Thus, the novel process for synthesizing 1-(mercaptomethyl)-cyclopropaneacetic acid provided by the present invention avoids the use of malodorous reagents such as thiolacetic acid and hydrogen sulfide derivatives, proceeds via solid intermediates which can be isolated and purified prior to further reaction, and avoids the use of a base hydrolysis as the final step in the process. The process according to the invention is therefore capable of producing 1-(mercaptomethyl)-cyclopropaneacetic acid of higher purity than known processes while using simpler techniques for handling reagents and for handling and purifying intermediates.

In another aspect, the present invention provides the novel intermediates 5-oxa-spiro[2.4]hept-6-ylideneamine and acid addition salts thereof and the corresponding 1-(halomethyl)-cyclopropaneacetamide, and a novel process for preparing these intermediates which essentially comprises the first step of the above-described process for preparation of 1-(mercaptomethyl)-cyclopropaneacetic acid.

In yet another aspect, the present invention provides the novel intermediate 1-(carbamimidoylsulfanylmethyl)-cyclopropaneacetamide and acid addition salts thereof, and a novel process for preparing this intermediate which essentially comprises the first two steps of the above-described synthesis for preparation of 1-(mercaptomethyl)-cyclopropaneacetic acid.

In yet another aspect, the present invention provides a novel process for preparing 1-(mercaptomethyl)-cyclopropaneacetic acid disulfide which essentially comprises the first three steps of the above-described synthesis for preparation of 1-(mercaptomethyl)-cyclopropaneacetic acid.

DETAILED DESCRIPTION OF PREFERRED EMBODIMENTS

The following is a detailed description of preferred processes according to the invention for preparing 1-(mercaptomethyl)-cyclopropaneacetic acid.

As mentioned above, the starting material in the process of the present invention is 1-(hydroxymethyl)-cyclopropaneacetonitrile, which is known in the art and may be readily prepared according to known processes. For example, U.S. Pat. No. 5,523,477 discloses a method for preparing 1-(hydroxymethyl)-cyclopropaneacetonitrile from 1,1-cyclopropanedimethanol.

In the first step of the process of the invention, shown below, 1-(hydroxymethyl)-cyclopropaneacetonitrile (I) is treated with an acid to form the corresponding imino ester salt (II), which is partially or completely converted to the corresponding halo-amide (III) under the reaction conditions.

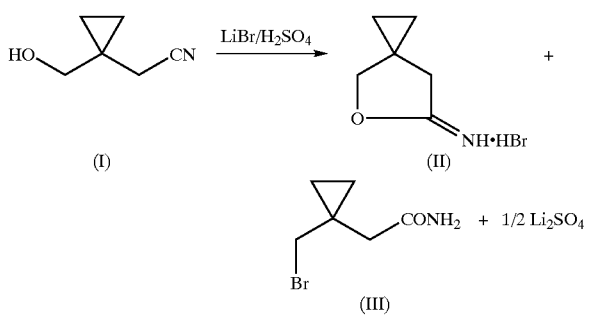

The reaction depicted above is an example of a Pinner Synthesis, generally described in Pinner et al., Ber. 10, 1889 (1877); 11, 4, 11475 (1878); 16, 352, 1643 (1883).

Preferred acids for the reaction with 1-(hydroxymethyl)-cyclopropaneacetonitrile include those selected from the group comprising HBr, HCl, LiBr/H$_2$SO$_4$, NaBr/ H$_2$SO$_4$, KBr/H$_2$SO$_4$, KCl/H$_2$SO$_4$, NaCl/H$_2$SO$_4$ or LiCl/H$_2$SO$_4$. It is preferred that about 0.5 to 2 molar equivalents of the acid are used.

The reaction is preferably conducted in an inert solvent or a mixture of solvents, with preferred inert solvents being selected from the group comprising ethyl acetate, isopropyl acetate, acetone, methyl ethtone, methyl isobutyl ketone, propanol, butanol, isopropanol and t-butanol. The reaction temperature preferably ranges from about −10° C. to about 25° C.

In a particularly preferred embodiment of the invention, the acid comprises LiBr(1–1.2 eq)/H$_2$SO$_4$ (0.5–0.65 eq) and the inert solvent comprises isopropyl acetate. This combination produces the bromide salt of the above imino ester intermediate (II) and the bromo amide intermediate (III).

Preferably the intermediates (II) and (III) are not isolated prior to further reaction. Isolation is unnecessary since both species react in a similar manner in the second step of the process, now described below.

The second step of the preferred process, depicted below, comprises reaction of the intermediates (II) and (III) with thiourea to give a salt of 1-(carbamimidoylsulfanylmethyl)-cyclopropaneacetamide (IV), also referred to herein as the "amide-isothiuronium salt".

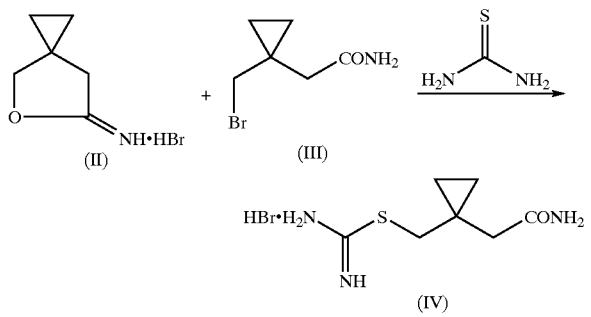

Preferably, the second step of the process comprises addition of from about 1 to about 1.5 molar equivalents of thiourea to the reaction mixture of step 1 containing the imidate salt (II) and/or the halo amide (III). The reaction is preferably carried out in an inert solvent or a mixture of inert solvents, with preferred solvents including those selected from the group comprising acetone, ethyl acetate, isopropyl acetate, isopropanol, ethanol and toluene. The reaction temperature is preferably maintained at between about 40° C. and the reflux temperatures of the solvent for a few hours. In a particularly preferred embodiment of the invention, the second step of the process is carried out in acetone at reflux.

After completion of the reaction, the reaction mixture is preferably cooled, resulting in precipitation of the amide-isothiuronium salt (IV) as a white to off-white solid precipitate along with inorganic salts produced during the first step of the. process. The yield of amide-isothiuronium salt (IV), calculated over the first two steps of the process, is typically from about 80% to about 94%.

In the third step of the preferred process, depicted below, the amide-isothiuronium salt (IV), which may also contain some inorganic salts produced during the first step of the process is first hydrolyzed under basic conditions.

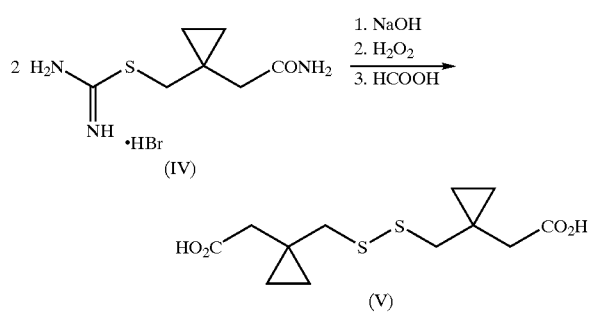

Preferred nucleohpiles for use in the hydrolysis include those selected from the group comprising alkali and alkaline earth metal hydroxides, for example, NaOH, LiOH, KOH, Ca(OH)$_2$, Ba(OH)$_2$ or quaternary ammonium hydroxides, with the use of alkali metal hydroxides being particularly preferred. The nucleophile is preferably used in excess, with 4.5 to 6.5 molar equivalents, and the reaction temperature preferably ranges from about 80° C. to about 110° C.

Hydrolysis of the amide-isothiuronium salt (IV) results in the formation of a 1-(mercaptomethyl)-cyclopropaneacetate salt (not shown), which is oxidized in situ to produce 1-[1-(carboxymethyl)-cyclopropanemethyldisulfanylmethyl]-cyclopropaneacetic acid, also referred to herein as 1-(mercaptomethyl)-cyclopropaneacetic acid disulfide, and having formula (V) shown above.

The oxidation is carried out using an oxidizing agent, preferably iodine or a peroxide selected from the group comprising hydrogen peroxide, t-butyl hydroperoxide and m-chloroperbenzoic acid. During the oxidation, the temperature of the reaction mixture is lowered to the range of about −5° to about 25° C. Particularly preferred conditions for the oxidation comprise the use of from about 0.55 to about 0.7 molar equivalents of hydrogen peroxide solution. After the oxidation is complete, the reaction mixture is acidified to a pH of between 3.5 to 4.0, preferably using an acid selected from the group comprising formic acid, acetic acid, citric acid, hydrochloric acid, dilute sulfuric acid, KHSO$_4$ and NaHSO$_4$. A particularly preferred acid is aqueous formic acid. Precipitates of 1-(mercaptomethyl)-cyclopropaneacetic acid disulfide (V) are isolated by filtration. The crude product isolated as such usually shows ≧98% area purity by HPLC. Recrystallization using a solvent or a mixture of solvents selected from water, methanol, ethanol, isopropanol, acetone, ethyl acetate, isopropyl acetate, toluene, heptane, hexane and pentane, gives pure (>99% area by HPLC) disulfide compound (V). A particularly preferred solvent system is water-isopropyl acetate-heptane. Activated carbon may be involved during the recrystallization. 1-(mercaptomethyl)-cyclopropaneacetic acid disulfide is obtained as a white or off-white solid in 75% to 89% yield.

In the final step of the process, depicted below, the 1-(mercaptomethyl)-cyclopropaneacetic acid disulfide (V) is reduced to the corresponding 1-(mercaptomethyl)-cyclopropaneacetic acid (VI) by treatment with a reducing agent.

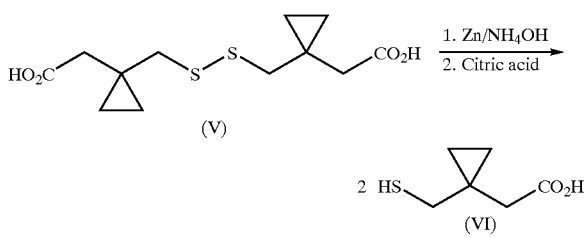

Preferred reducing agents for use in the fourth step of the process include zinc/ammonium hydroxide and zinc/acetic acid. The system of zinc (1–1.3 molar equivalent)/ammonium hydroxide (4.5–5.5 molar equivalent) is particularly preferred. The reaction temperature preferably ranges from about 20° C. to about 65° C., more preferably from about 25° C. to about 55° C. Due to the sensitivity of the 1-(mercaptomethyl)-cyclopropaneacetic acid to oxidation, the reduction is preferably carried out under an inert atmosphere such as nitrogen or argon, and deoxygenated solvents and solutions are preferably used for the work up.

Upon completion of the reaction as detected by HPLC, the reaction mixture is filtered for clarification and the filtrate is acidified at lower temperatures, for example, from −5° to 25° C. in order to achieve a pH of between 3.3 and 4. Suitable acids include formic acid, acetic acid, citric acid, hydrochloric acid, dilute sulphuric acid, $KHSO_4$ and $NaHSO_4$. The presence or absence of an organic solvent such as ethyl acetate, isopropyl acetate, methyl t-butyl ether, toluene or heptane does not affect the acidification. A particularly preferred combination of conditions comprises the use of citric acid/isopropyl acetate for the acidification at between −3° to 10° C. until a pH of between 3.3 and 3.8 is obtained.

The 1-(mercaptomethyl)-cyclopropaneacetic acid obtained from the fourth step is then extracted with an organic solvent or mixture of solvents, preferably selected from the group comprising ethyl acetate, isopropyl acetate, methyl t-butyl ether, toluene or heptane. The organic layer is washed with water or aqueous sodium chloride or ammonium chloride solutions. It is then concentrated under reduced pressure at a temperature below 40° C. to remove the solvent and traces of water. Heptane or hexane is then added and the mixture is slightly warmed (30–45° C.) for the dissolution of the product. A filtration is performed to remove any insoluble impurities and salts. The filtrate is further concentrated in vacuo. Upon cooling, the product crystallizes. Isolation by filtration at between −10° to 0° C. followed by washes with cold heptane or hexane gives the 1-(mercaptomethyl)-cyclopropaneacetic acid as a white crystalline solid. The purity of the compound is usually 99.5% to 100% area by HPLC and the yield is from 70% to 88%. Apart from the possible presence of the corresponding disulfide, no single impurity is higher than 0.05% area by HPLC. Although generally not necessary, the compound could be purified by recrystallization with or without activated carbon in a deoxygenated solvent or a mixture of solvents, preferably selected from heptane, hexane, ethyl acetate, isopopyl acetate or methyl t-butyl ether.

Thus the present invention enables the preparation of highly pure 1-(mercaptomethyl)-cyclopropaneacetic acid via easily isolable and purifiable stable solid intermediates. Neither of the isolated intermediates, i.e. the amide-isothiuronium salt (IV) or the 1-(mercaptomethyl)-cyclopropaneacetic acid disulfide (V), present odour problems.

The invention is further illustrated by the following non-limiting examples. All procedures are carried out under an inert atmosphere (nitrogen).

EXAMPLE 1

Preparation of 5-oxa-spiro[2.4]hept-6-ylideneamine-HBr and 1-(bromomethyl)-cyclopropaneacetamide This example describes a method for preparing a preferred imino ester acid addition salt and the corresponding halo-amide by the following step which is more generally described above as step 1.

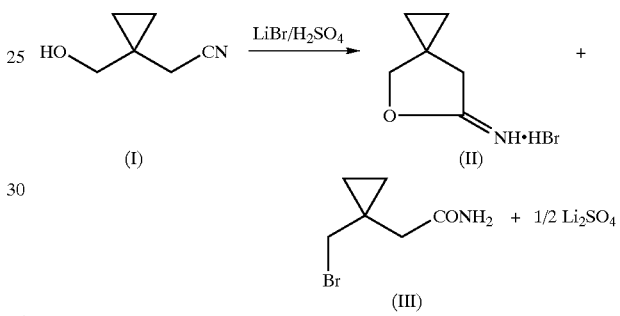

A 500 mL 3-neck round bottomed flask was equipped with a water condenser, an addition funnel and a thermometer. The system was linked to a caustic scrubber. To the flask was charged 36.56 g of 1-(hydroxymethyl)-cyclopropaneacetonitrile, 207 mL of isopropyl acetate and 31.30 g of lithium bromide. The mixture was cooled to between −5 and −10° C. Under agitation, via the addition funnel, 10.1 mL of concentrated (96%) sulfuric acid was slowly added to the suspension while maintaining the internal temperature below 10° C. After the addition, the reaction mixture was stirred at between 0° C. and 10° C. for 1 hour and then warmed to 20–25° C. and stirred for about 2 hours. Proton NMR was taken on a sample of the reaction confirming the disappearence of the 1-(hydroxymethyl)-cyclopropaneacetonitrile. The reaction mixture was then degassed for 45 min under vacuum purge to remove the small excess of HBr formed during the reaction. Then the suspension was concentrated in vacuo at below 45° C. to about 95 mL and was charged with 220 mL of acetone. The suspension was concentrated again to about 230 mL.

EXAMPLE 2

Preparation of 1-(carbamimidoylsulfanylmethyl)-cyclopropaneacetamide•HBr (amide-isothiuronium HBr salt)

This example describes a method for preparing amide-isothiuronium salt (IV) from the imino ester acid addition salt and the halo-amide produced in Example 1. The amide-isothiuronium salt (IV) is prepared by the following method which is generally described above as step 2.

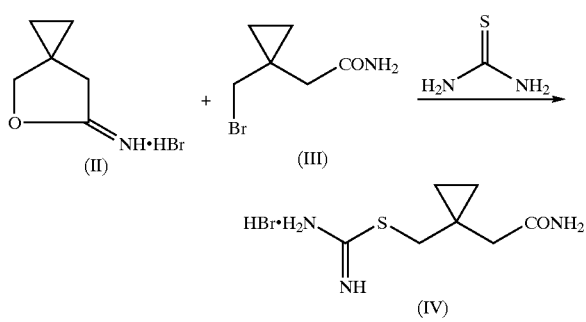

To the concentrated suspension produced in Example 1 was added 25.1 g of thiourea and the resulting mixture was heated to reflux and aged for a period of about 6 h until completion of reaction as detected by proton NMR. The reaction mixture was cooled to room temperature then further cooled to about −5° C. After stirring at this temperature for about 1 hour, the suspension was filtered and the solid was washed with 3×55 mL of cold acetone. After drying, a white solid was obtained. The solid (91.87 g) contained 19.89 g of lithium sulfate (100% of theory) and 71.98 g (83% of theory) of 1-(carbamimidoylsulfanylmethyl)-cyclopropaneacetamide•HBr. $^1$H NMR (DMSO-d6): δ9.26 (s,4H), 7.64(s,1H), 7.17(s,]H), 3.28(s,2H), 2.14(s,2H), 0.56 (s,4H). $^{13}$C NMR (DMSO-d6): δ173.25(1C), 170.02(1C), 39.19(1C), 37.97(1C), 17.08(1C), 11.85(2C).

EXAMPLE 3

Preparation of 1-[1-(carboxymethyl)-cyclopropanemethyldisulfanylmethyl]-cyclopropaneacetic acid (1-(mercaptomethyl)-cyclopropaneacetic acid disulfide)

This example describes a preferred process for preparing the disulfide (V) from the amide-isothiuronium salt (IV), referred to above as the third step of the process.

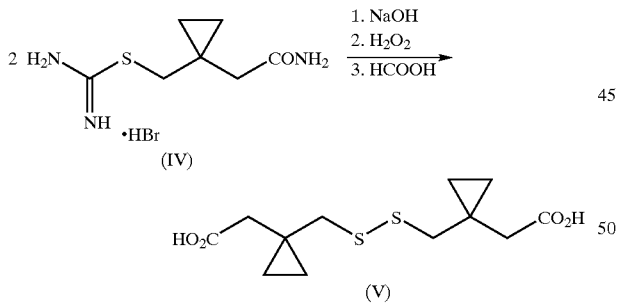

A 500 mL 3-neck round bottomed flask was fitted with a water condenser, a thermometer and a magnetic stirrer. The condenser was linked to a scrubber containing dilute sulfuric acid. To the flask was charged 96 mL of water, 76.92 g of 50% sodium hydroxide solution and 57.2 g of a solid containing 45.2 g of the amide-isothiuronium HBr salt and 12.0 g of lithium sulfate prepared as described in Examples 2 and 1, respectively. The suspension was heated to 97–100° C. under slight negative pressure scrubbing for a period of about 12 hours. Upon completion of the reaction as detected by HPLC, the reaction mixture was cooled to room temperatures. A filtration was performed to remove the inorganic salts that precipitated. 2×10 mL of water were used to wash the filter cake and were incorporated with the filtrate. The filtrate was cooled to between −5° C. and 0° C. under agitation with a mechanical stirrer. While maintaining the temperature below 5° C., a solution of hydrogen peroxide prepared from 10.5 g of 30% hydrogen peroxide and 17.5 mL of water was slowly added. The solution was stirred at this temperature for 2 hours after the addition, after which time HPLC showed that the oxidation was complete. The reaction mixture was further diluted with 171 mL of water. While maintaining the agitation and a temperature between −5° C. and 5° C., a solution of 55% formic acid was gradually added to lower the pH to between 3.5 and 4.0. A pH of 3.85 was obtained with the addition of 55 mL of the acid solution. A white suspension was observed which was allowed to warm up to room temperature and was isolated by filtration.

To the 40.32 g of the wet solid (with 45% water content) was added 4 mL of water, 67 mL of isopropyl acetate and 1.2 g of activated carbon. The mixture was heated to reflux to dissolve the compound and then a hot filtration was performed to remove the carbon. The filter cake was washed with 2×10 mL hot isopropyl acetate and the combined filtrate was cooled under agitation to about 40–50° C. 47 mL of heptane was added under agitation. Cooling continued to a temperature between 0° C. and 5° C. and the suspension was further agitated for about 1 hour. A white to off-white solid was isolated after filtration and washed (2×20 mL water followed by 2×20 mL of a cold mixture prepared from 30 mL of heptane and 10 mL of isopropyl acetate). After air drying at a temperature no greater than 50° C., 19.79 g (80.9% of theory) of 1-(mercaptomethyl)-cyclopropaneacetic acid disulfide was obtained. HPLC showed 99.89% area purity. The compound had a melting point of 135.85° C. by DSC. $^1$H NMR (DMSO-d6): δ12.08 (s,2H), 2.89(s,4H), 2.32(s,4H), 0.52(m,8H). $^{13}$C NMR (DMSO-d6): δ173.03(2C), 47.75(2C), 39.34(2C), 17.42 (2C), 12.16(4C). (The melting point and $^1$H NMR data correspond to previous descriptions in EP0641775.

EXAMPLE 4

Preparation of 1-(mercaptomethyl)-cyclopropaneacetic acid

This example describes a preferred process for preparing 1-(mercaptomethyl)-cyclopropaneacetic acid from the corresponding disulfide (V), more generally described above as the fourth step of the process.

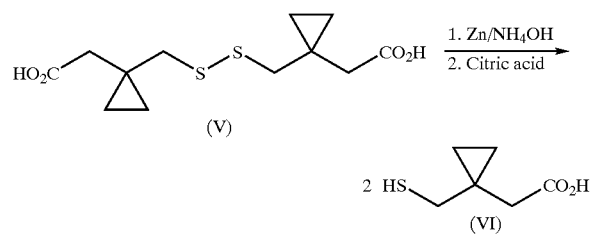

All solvents and solutions used in the procedure were deoxygenated with the exception of the ammonium hydroxide solution. Nitrogen atmosphere protection was used throughout the procedure.

A IL 3-neck round bottomed flask was fitted with a water condenser, a thermometer and a mechanical stirrer. To the flask was charged with 80.0 g of of 1-(mercaptomethyl)-cyclopropaneacetic acid disulfide (V) produced as described in Example 3, purged with nitrogen, and was then charged with 80 mL of water and 19.8 g of Zinc powder. Under agitation, in the presence of a 20° C. water bath, 79 mL of 30% ammonium hydroxide solution was slowly added while maintaining the internal temperature below 45° C. Stirring was continued at 30–45° C. for about 3.5 h when HPLC confirmed a complete transformation. A greyish solution with traces of zinc powder was observed.

The reaction mixture was filtered to remove the residual solid. The filtrate was cooled to about −3° C. With good agitation, 357 mL of 50% citric acid solution was added over about 50 min while maintaining the internal temperature below 5° C. A final pH of 3.51 and a white suspension were observed. The mixture was allowed to warm to room temperature and was extracted with 2×240 mL of isopropyl acetate. The combined organic layers were washed once with 80 mL of water and the solvent was evaporated in vacuo at below 40° C. to give an oil residue. The residue was charged with 282 mL of heptane, heated to 35–40° C., and the solution obtained was filtered once more to remove any traces of salts. The solvent was evaporated again under similar conditions. Another portion of 282 mL of heptane was charged and the mixture was concentrated to about 220 mL. The resulting mixture was heated under agitation to about 40° C. in order to obtain a homogeneous solution then it was cooled to room temperature and further cooled to between −10 and −15° C. Agitation continued at this temperature range for 1 h then the white suspension was filtered. The solid was washed with 60 mL of cold heptane and was dried under a flow of nitrogen at room temperatures. The yield of 1-(mercaptomethyl)-cyclopropaneacetic acid was 70.87 g, which corresponds to 88% of theory. The compound had a melting point of 43.8° C. by DSC and 100% area purity by HPLC. $^1$H NMR (CDCl$_3$): δ11.72(s,1H), 2.62(d,2H), 2.50(s,2H), 1.35(t,1H), 0.56(m,4H). $^{13}$C NMR (CDCl$_3$): δ178.86(1C), 39.07(1C), 32.78(1C), 19.88(1C), 13.13(2C). (The melting point and $^1$H NMR data correspond to previous descriptions in EP0641775.) The compound was sealed under nitrogen and was stored in a refrigerator.

What is claimed is:

1. A process for preparing 1-(mercaptomethyl)-cyclopropaneacetic acid, comprising:
   (a) converting 1-(hydroxymethyl)-cyclopropaneacetonitrile to 5-oxa-spiro[2.4]hept-6-ylideneamine, an acid addition salt thereof, and/or 1-(halomethyl)-cyclopropaneacetamide by treatment of said 1-(hydroxymethyl)-cyclopropaneacetonitrile with an acid;
   (b) reaction of said 5-oxa-spiro[2.4]hept-6-ylideneamine, said acid addition salt thereof, and/or said 1-(halomethyl)-cyclopropaneacetamide with thiourea to produce 1-(carbamimidoylsulfanylmethyl)-cyclopropaneacetamide or an acid addition salt thereof;
   (c) converting said 1-(carbamimidoylsulfanylmethyl)-cyclopropaneacetamide to 1-(mercaptomethyl)-cyclopropaneacetic acid disulfide by hydrolysis of said 1-(carbamimidoylsulfanylmethyl)-cyclopropaneacetamide, followed by oxidation to produce said disulfide; and
   (d) reduction of said disulfide to produce said 1-(mercaptomethyl)-cyclopropaneacetic acid.

2. The process of claim 1, wherein said 5-oxa-spiro[2.4]hept-6-ylideneamine, said acid addition salt thereof, and/or said 1-(halomethyl)-cyclopropaneacetamide are not isolated from the reaction mixture of step (b) prior to step (c).

3. The process of claim 1, wherein one or more of said 5-oxa-spiro[2.4]hept-6-ylideneamine, said acid addition salt thereof, and said 1-(halomethyl)-cyclopropaneacetamide are isolated from the reaction mixture of step (b) prior to step (c).

4. The process of claim 1, further comprising isolation of said 1-(carbamimidoylsulfanylmethyl)-cyclopropaneacetamide prior to step (c).

5. The process of claim 4, further comprising purification of said 1-(carbamimidoylsulfanylmethyl)-cyclopropaneacetamide prior to step (c).

6. The process of claim 1, further comprising isolation of said disulfide prior to step (d).

7. The process of claim 5, further comprising purification of said disulfide prior to step (d).

8. The process of claim 1, wherein the acid used in step (a) is selected from the group comprising HBr, HCl, LiBr/H$_2$SO$_4$, NaBr/H$_2$SO$_4$, KBr/H$_2$SO$_4$, KCl/H$_2$SO$_4$, NaCl/H$_2$SO$_4$ or LiCl/H$_2$SO$_4$.

9. The process of claim 8, wherein the acid is LiBr/H$_2$SO$_4$.

10. The process of claim 1, wherein said hydrolysis of step (c) is carried out using a nucleophile selected from the group comprising alkali and alkaline earth metal hydroxides.

11. The process of claim 1, wherein said oxidation of step (c) is carried out using an oxidizing agent selected from the group comprising iodine and peroxides.

12. The process of claim 1, wherein said reduction of step (d) is carried out using a reducing agent selected from the group comprising zinc/ammonium hydroxide and zinc/acetic acid.

13. The compound 5-oxa-spiro[2.4]hept-6-ylideneamine or an acid addition salt thereof.

14. The compound 1-(halomethyl)-cyclopropaneacetamide or an acid addition salt thereof.

15. A process for preparing 5-oxa-spiro[2.4]hept-6-ylideneamine, an acid addition salt thereof, and 1-(halomethyl)-cyclopropaneacetamide, comprising treatment of 1-(hydroxymethyl)-cyclopropaneacetonitrile with an acid.

16. The compound 1-(carbamimidoylsulfanylmethyl)-cyclopropaneacetamide or an acid addition salt thereof.

17. A process for preparing 1-(carbamimidoylsulfanylmethyl)-cyclopropaneacetamide or an acid addition salt thereof by treatment of 1-(hydroxymethyl)-cyclopropaneacetonitrile with an acid, followed by reaction with thiourea.

18. A process for preparing 1-(mercaptomethyl)-cyclopropaneacetic acid disulfide, comprising:
   (a) converting 1-(hydroxymethyl)-cyclopropaneacetonitrile to 1-(carbamimidoylsulfanylmethyl)-cyclopropaneacetamide or an acid addition salt thereof by treatment of said 1-(hydroxymethyl)-cyclopropaneacetonitrile with an acid, followed by reaction with thiourea to produce said 1-(carbamimidoylsulfanylmethyl)-cyclopropaneacetamide; and
   (b) converting said 1-(carbamimidoylsulfanylmethyl)-cyclopropaneacetamide to said disulfide by hydrolysis of said 1-(carbamimidoylsulfanylmethyl)-cyclopropaneacetamide, followed by oxidation to produce said disulfide.

* * * * *